US 6,596,711 B1
Jul. 22, 2003

(12) United States Patent
Amin et al.

(10) Patent No.: US 6,596,711 B1
(45) Date of Patent: Jul. 22, 2003

(54) (AMINOPROPYL)METHYLPHOSPHINIC ACIDS

(75) Inventors: Kosrat Amin, Mölndal (SE); Thomas Elebring, Pixbo (SE); Peter Guzzo, Niskayuna, NY (US); Thomas Olsson, Torslanda (SE); Marianne Swanson, Mölndal (SE); Sverker Von Unge, Fjärås (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/786,220

(22) PCT Filed: Dec. 4, 2000

(86) PCT No.: PCT/SE00/02427

§ 371 (c)(1),
(2), (4) Date: Mar. 1, 2001

(87) PCT Pub. No.: WO01/41743

PCT Pub. Date: Jun. 14, 2001

(30) Foreign Application Priority Data

Dec. 9, 1999 (SE) .................................................. 9904507

(51) Int. Cl.$^7$ .............................. A61K 31/66; C07F 9/30
(52) U.S. Cl. ...................... 514/114; 514/120; 514/129; 558/169; 558/178; 562/11
(58) Field of Search ................. 558/169, 178; 562/11; 514/114, 120, 129

(56) References Cited

U.S. PATENT DOCUMENTS

| | | | |
|---|---|---|---|
| 5,036,057 A | | 7/1991 | Martin .................. 514/54 |
| 5,281,747 A | * | 1/1994 | Hall et al. .............. 562/11 |
| 5,461,040 A | * | 10/1995 | Hall et al. .............. 514/114 |
| 5,567,840 A | * | 10/1996 | Hall et al. .............. 562/11 |
| 6,117,908 A | | 9/2000 | Andrews et al. ......... 514/567 |

FOREIGN PATENT DOCUMENTS

| | | |
|---|---|---|
| CH | 449046 | 4/1968 |
| EP | 0181833 | 5/1986 |
| EP | 0356128 | 2/1990 |
| EP | 0399949 | 11/1990 |
| EP | 0463969 | 1/1992 |
| FR | 2722192 | 1/1996 |
| WO | 8704077 | 7/1987 |
| WO | 9611680 | 4/1996 |
| WO | 9811885 | 3/1998 |

OTHER PUBLICATIONS

Froestl, et al. (1995), J. Med. Chem., 38, 3297–3312.
Zukin, et al. (1974), Proc. Natl. Acad. USA 71, 4802–4807.
Olpe et al. (1990), Eur. J. Pharmacol. 187, 27–38.
Holloway & Dent (1990), Gastroenterol. Clin. N. Amer. 19, 517–535.

* cited by examiner

Primary Examiner—Joseph K. McKane
Assistant Examiner—Kamal Saeed
(74) Attorney, Agent, or Firm—White & Case LLP

(57) ABSTRACT

Novel compounds of formula I, with the exception of
  i) the racemate of (3-amino-2-hydroxypropyl) methylphosphinic acid;
  ii) (S)-(3-amino-2-hydroxypropyl)methylphosphinic acid;
  iii) (R)-(3-amino-2-hydroxypropyl)methylphosphinic acid;
  iv) (3-amino-2-hydroxypropyl)difluoromethylphosphinic acid; and
  v) (3-amino-2-oxopropyl)methylphosphinic acid,
having affinity to one or more $GABA_B$ receptors, their pharmaceutically acceptable salts, solvates and stereoisomers, as well as a process for their preparation, pharmaceutical compositions containing said therapeutically active compounds and the use of said active compounds in therapy.

(I)

$$R_4 \diagup \underset{R_3}{\overset{H}{N}} \diagdown \underset{}{\overset{R_2}{C}} \diagdown \underset{R_1}{\overset{}{C}} \diagdown \underset{OH}{\overset{O}{P}} - R_5$$

11 Claims, No Drawings

(AMINOPROPYL)METHYLPHOSPHINIC ACIDS

This application is a 371 of PCT/SE00/02427 filed Dec. 4, 2000.

FIELD OF THE INVENTION

The present invention is related to novel compounds having affinity to one or more $GABA_B$ receptors, as well as to their pharmaceutically acceptable salts, solvates and stereoisomers. The invention is also related to processes for their preparation, pharmaceutical compositions containing said therapeutically active compounds and to the use of said active compounds in therapy.

BACKGROUND AND PRIOR ART

Reflux

Gastro-oesophageal reflux disease (GORD) is the most prevalent upper gastrointestinal tract disease. Current therapy has aimed at reducing gastric acid secretion, or at reducing oesophageal acid exposure by enhancing oesophageal clearance, lower oesophageal sphincter tone and gastric emptying. The major mechanism behind reflux has earlier been considered to depend on a hypotonic lower oesophageal sphincter. However recent research (e.g. Holloway & Dent (1990) Gastroenterol. Clin. N. Amer. 19, 517–535) has shown that most reflux episodes occur during transient lower oesophageal sphincter relaxations, hereinafter referred to as TLOSR, i.e. relaxations not triggered by swallows. It has also been shown that gastric acid secretion usually is normal in patients with GORD.

Consequently, there is a need for compounds which reduce the incidence of TLOSR and thereby prevent reflux.

A pharmaceutical composition comprising a local anaesthetic, adapted to inhibit relaxation of the lower oesophageal sphicter is disclosed in WO 87/04077 and in U.S. Pat. No. 5,036,057. Recently $GABA_B$-receptor agonists have been shown to inhibit TLOSR, as disclosed in WO 98/11885.

$GABA_B$ Receptor Agonists

GABA (4-aminobutanoic acid) is an endogenous neurotransmitter in the central and peripheral nervous systems. Receptors for GABA have traditionally been divided into $GABA_A$ and $GABA_B$ receptor subtypes. $GABA_B$ receptors belong to the superfamily of G-protein coupled receptors. $GABA_B$ receptor agonists are being described as being of use in the treatment of CNS disorders, such as muscle relaxation in spinal spasticity, cardiovascular disorders, asthma, gut motility disorders such as irritable bowel syndrome (IBS) and as prokinetic and anti-tussive agents. $GABA_B$ receptor agonists have also been disclosed as useful in the treatment of emesis (WO 96/11680) and recently, as mentioned above, in the inhibition of TLOSR (WO 98/11885).

The most studied $GABA_B$ receptor agonist is baclofen (4-amino-3-(chlorophenyl)butanoic acid) disclosed in the Swiss patent No. CH 449,046. Baclofen has for several years been used as an antispastic agent. EP 0356128 describes the use of the specific compound (3-aminopropyl) methylphosphinic acid, as a potent $GABA_B$ receptor agonist, in therapy. EP 0181833 discloses substituted 3-aminopropylphosphinic acids which are found to have very high affinities towards $GABA_B$ receptor sites. In analogy to baclofen, the compounds can be used as for instance muscle relaxants. EP 0399949 discloses derivatives of (3-aminopropyl)methylphosphinic acid which are described as potent $GABA_B$ receptor agonists. These compounds are stated to be useful as muscle relaxants. EP 0463969 and FR 2722192 are both applications related to 4-aminobutanoic acid derivatives having different heterocyclic substituents at the 3-carbon of the butyl chain. Structure-activity relationships of several phosphinic acid analogues with respect to their affinities to the $GABA_B$ receptor as well as their muscle relaxant effect are discussed in J. Med. Chem. (1995), 38, 3297–3312. The conclusion in said article is that considerably stronger muscle relaxation could be achieved with the (S)-enantiomer of 3-amino-2-hydroxy-propylmethylphosphinic acid than with baclofen and without the occurrence of unwanted CNS effects.

OUTLINE OF THE INVENTION

The present invention provides novel compounds of the formula I

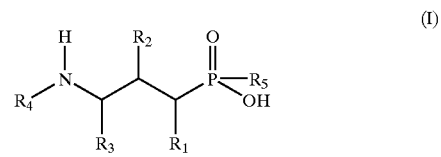

(I)

wherein $R_1$ represents hydrogen, hydroxy, lower alkyl, lower alkoxy or halogen;

$R_2$ represents hydroxy, mercapto, halogen or an oxo group;

$R_3$ represents hydrogen or lower alkyl (optionally substituted with hydroxy, mercapto, lower alkoxy, aryl or lower thioalkoxy);

$R_4$ represents hydrogen, lower alkyl (optionally substituted with aryl) or aryl;

$R_5$ represents methyl, fluoromethyl, difluoromethyl or trifluorormethyl;

and pharmaceutically acceptable salts, solvates and the stereoisomers thereof, with the exceptions of:

i) the racemate of (3-amino-2-hydroxypropyl) methylphosphinic acid, ii) (S)-(3-amino-2-hydroxypropyl)methylphosphinic acid, iii) (R)-(3-amino-2-hydroxypropyl)methylphosphinic acid, iv) (3-amino-2-hydroxypropyl)difluoromethylphosphinic acid, and v) (3-amino-2-oxopropyl)methylphosphinic acid.

Preferably the compound is one of (3-amino-2-fluoropropyl)(methyl)phosphinic acid, (2R)-(3-amino-2-fluoropropyl)(methyl)phosphinic acid, (2S)-(3-amino-2-fluoropropyl)(methyl)phosphinic acid, (3-amino-2-fluoro-1-methylpropyl)(methyl)phosphinic acid or pharmaceutically acceptable salts, solvates or the stereoisomers thereof.

Within the scope of the invention, it is to be understood that when $R_2$ is an oxo group the bond between $R_2$ and the carbon is a double bond.

Furthermore, within the scope of the invention, it is to be understood by "lower" radicals and compounds, for example, those having up to and including 7, especially up to and including 4, carbon atoms. Also the general terms have the following meanings:

Lower alkyl is, for example, $C_1$–$C_4$ alkyl, such as methyl, ethyl, n-propyl or n-butyl, also isopropyl, isobutyl, secondary butyl or tertiary butyl, but may also be a $C_5$–$C_7$ alkyl group such as a pentyl, hexyl or heptyl group.

Lower alkoxy is, for example, $C_1$–$C_4$ alkoxy, such as methoxy, ethoxy, n-propoxy or n-butoxy, also isopropoxy, isobutoxy, secondary butoxy or tertiary butoxy, but may also be a $C_5$–$C_7$ alkoxy group, such as a pentoxy, hexoxy or heptoxy group.

Lower thioalkoxy is, for example, $C_1$–$C_4$ thioalkoxy, such as thiomethoxy, thioethoxy, n-thiopropoxy or n-thiobutoxy, also thioisopropoxy, thioisobutoxy, secondary thiobutoxy or tertiary thiobutoxy, but may also be a $C_5$–$C_7$ thioalkoxy group, such as a thiopentoxy, thiohexoxy or thioheptoxy group.

Halogen is halogen of an atomic number up to and including 35, such as flourine or chlorine, and less prefered bromine.

The compounds according to formula I of the invention are of amphoteric nature and may be presented in the form of internal salts. They can also form acid addition salts and salts with bases. Such salts are particularly pharmaceutically acceptable acid addition salts, as well as pharmaceutically acceptable salts formed with bases. Suitable acids for the formation of such salts include, for example, mineral acids such as hydrochloric, hydrobromic, sulfuric, or phosphoric acid or organic acids such as sulfonic acids and carboxylic acids. Salts with bases are, for example, alkali metal salts, e.g. sodium or potassium salts, or alkaline earth metal salts, e.g. calcium or magnesium salts as well as ammonium salts, such as those with ammonia or organic amines. The salts may be prepared by conventional methods.

When one or more stereocentre is present in the molecule, the compounds according to formula I can be in the form of a stereoisomeric mixture, i.e. a mixture of diastereomers and/or enantiomers, or in the form of the single stereoisomers, i.e. the single enantiomer and/or diastereomer. The present compounds can also be in the form of solvates, e.g. hydrates.

All of the compounds according to the formula I can be used for the inhibition of TLOSR, and thus for the treatment of gastro-oesophageal reflux disease. The said inhibition of TLOSR also implies that all of the compounds of formula I can be used for the treatment of regurgitation in infants. Effective management of regurgitation in infants would be an important way of managing failure to thrive due to excessive loss of ingested nutrient. Furthermore the novel compounds can be used for the treatment of GORD- or non-GORD related asthma, belching, coughing, pain, cocaine addiction, hiccups, IBS, dyspepsia, emesis and nociception.

The present invention provides compounds having surprisingly high potencies and/or therapeutic index.

Preparation

The compounds according to formula I of the present invention may be prepared by one of the following methods.

A) A compound of formula II

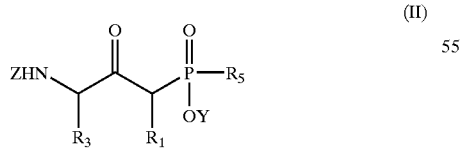

(II)

in which $R_1$, $R_3$ and $R_5$ are as defined above in formula I, Z is a protecting group such as t-butyloxycarbonyl and Y is hydrogen or a protecting group such as lower alkyl, which compound of formula II may have been synthesized by a condensation reaction according to Scheme 1 employing an appropriate N-protected amino acid ester in which $R_3$ is as defined above in formula I, W is a protecting group such as lower alkyl and Z is as defined in formula II, and a suitable protected phosphinic acid derivative in which $R_1$ and $R_5$ is as defined above in formula I, Y is as defined in formula II, and a base such as lithium diisopropylamide, Scheme 1

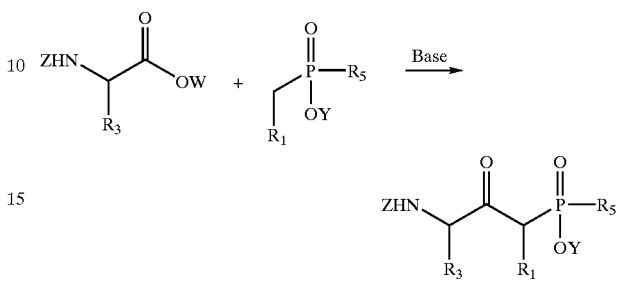

a) converted optionally by an N-alkylation reaction in order to introduce $R_4$ if $R_4$ is desired to be not equal to hydrogen, and thereafter a hydrolytic reaction to obtain a compound of formula III

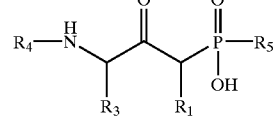

(III)

wherein $R_1$, $R_3$, $R_4$ and $R_5$ are as defined above in formula I, and optionally convert the above resulting compound III into another chemical compound of the formula III and/or sepatate a resulting mixture of isomers into the individual isomers and/or convert a resulting salt into the free compound of the formula III and/or into another salt and/or convert a resulting free compound of the formula III into a salt to correspond to the above definition, or b) converted by a reductive reaction, optionally an N-alkylation reaction if $R_4$ is desired to be not equal to hydrogen, and finally a hydrolytic reaction to a compound of formula IV

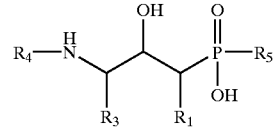

(IV)

wherein $R_1$, $R_3$, $R_4$ and $R_5$ are as defined above in formula I, and optionally convert the above resulting compound IV into another chemical compound of the formula IV and/or sepatate a resulting mixture of isomers into the individual isomers and/or convert a resulting salt into the free compound of the formula IV and/or into another salt and/or convert a resulting free compound of the formula IV into a salt to correspond to the above definition, or c) converted by a reductive reaction followed by a deoxohalogenation reaction, optionally an N-alkylation reaction in order to introduce $R_4$ if $R_4$ is desired to be not equal to hydrogen, and finally a hydrolytic reaction to obtain a compound of formula VI

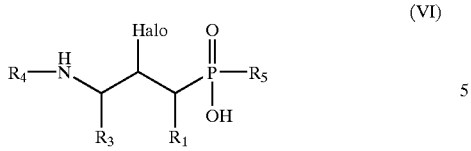

(VI)

wherein $R_1$, $R_3$ and $R_4$ are as defined above in formula I and Halo is a halogen atom, and optionally convert the above resulting compound VI into another chemical compound of the formula VI and/or sepatate a resulting mixture of isomers into the individual isomers and/or convert a resulting salt into the free compound of the formula VI and/or into another salt and/or convert a resulting free compound of the formula VI into a salt to correspond to the above definition;

or B) a compound of formula VII

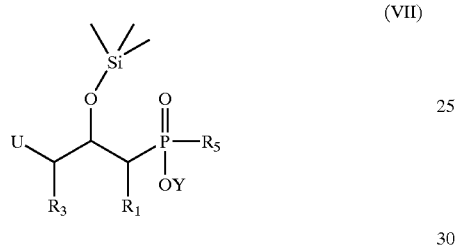

(VII)

in which $R_1$, $R_3$ and $R_5$ are as defined above in formula I, U is a group that can be converted to a —$NH_2$ group, and Y is hydrogen or a protecting group such as lower alkyl, which compound VII may have been synthesized by a condensation reaction according to Scheme 2 employing an 2,3-epoxypropyl derivative, such as an appropriate N-protected 2,3-epoxypropylamine derivative or an epichlorohydrin derivative, in which $R_1$ and $R_3$ is as defined above in formula I, and a suitable protected phosphinic acid derivative activated by O-silylation, in which $R_5$ and Y are as defined in formula VII, and a Lewis acid such as anhydrous $ZnCl_2$, Scheme 2

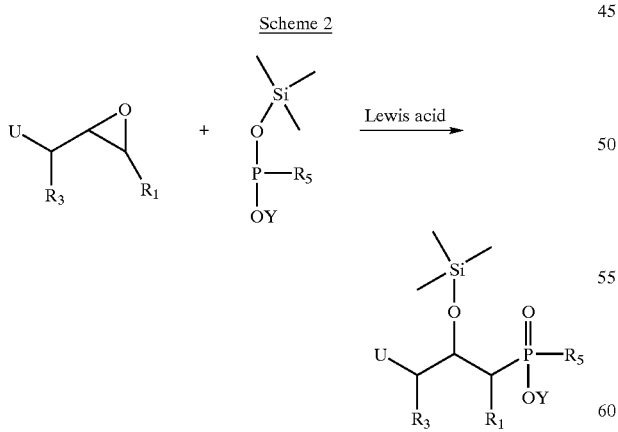

is a) converted by a reaction where the trimethylsilyl group is replaced by a hydrogen atom, a reaction where the U group as defined in formula VII is converted to —$NHR_4$ wherein $R_4$ is as defined above in formula I, and finally a hydrolytic reaction to obtain a compound of formula IV

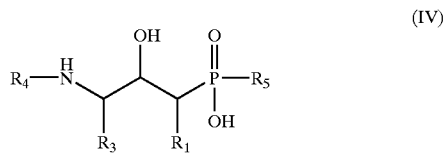

(IV)

wherein $R_1$, $R_3$, $R_4$ and $R_5$ are as defined above in formula I, and optionally convert the above resulting compound IV into another chemical compound of the formula IV and/or sepatate a resulting mixture of isomers into the individual isomers and/or convert a resulting salt into the free compound of the formula IV and/or into another salt and/or convert a resulting free compound of the formula IV into a salt to correspond to the above definition, or b) converted by a reaction where the trimethylsilyl group is replaced by hydrogen, an oxidative reaction, a reaction where the U group as defined in formula VII is converted to —$NHR_4$ wherein $R_4$ is as defined above in formula I, and finally a hydrolytic reaction to obtain a compound of formula III

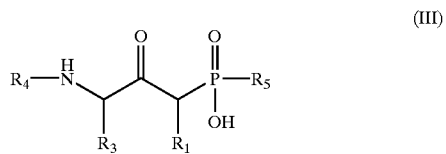

(III)

wherein $R_1$, $R_3$, $R_4$ and $R_5$ are as defined above in formula I, and optionally convert the above resulting compound III into another chemical compound of the formula III and/or sepatate a resulting mixture of isomers into the individual isomers and/or convert a resulting salt into the free compound of the formula III and/or into another salt and/or convert a resulting free compound of the formula III into a salt to correspond to the above definition, or c) converted by a reaction where the trimethylsilyl group is replaced by hydrogen, a deoxohalogenation reaction, a reaction where the U group as defined in formula VII is converted to —$NHR_4$ wherein $R_4$ is as defined above in formula I, and finally a hydrolytic reaction to obtain a compound of formula VI

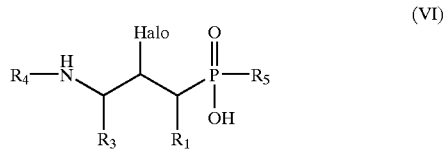

(VI)

wherein $R_1$, $R_3$, $R_4$ and $R_5$ are as defined above in formula I, and Halo is a halogen atom, and optionally convert the above resulting compound VI into another chemical compound of the formula VI and/or sepatate a resulting mixture of isomers into the individual isomers and/or convert a resulting salt into the free compound of the formula VI and/or into another salt and/or convert a resulting free compound of the formula VI into a salt to correspond to the above definition;

or C) a compound of formula VIII

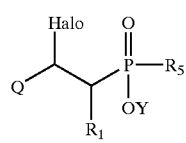

(VIII)

in which $R_1$ and $R_5$ are as defined above in formula I, Q is an electron-withdrawing group, such as for instance —CN or —CO$_2$Et which can be converted to a —CH$_2$NH$_2$ group, and Y is hydrogen or a protecting group such as lower alkyl, and Halo is a halogen atom, which compound of formula VIII may have been synthesized by an addition reaction according to Scheme 3 employing an unsaturated compound in which $R_1$ is as defined above in formula I, Q and Halo are as defined in formula VIII, and a suitable protected phosphinic acid derivative activated by O-silylation, in which $R_5$ and Y are as defined in formula VIII, Scheme 3

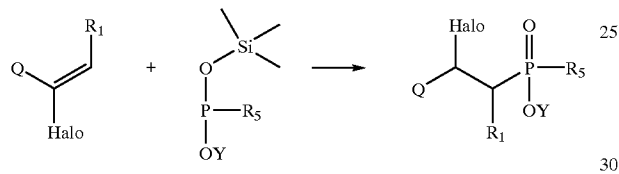

is converted by a reaction where the Q group is being converted to —NHR$_4$ wherein $R_4$ is as defined above in formula I, and a hydrolytic reaction to obtain a compound of formula IX

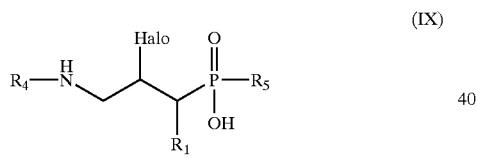

(IX)

wherein $R_1$ and $R_4$ are as defined above in formula I and Halo is a halogen atom, and optionally convert the above resulting compound IX into another chemical compound of the formula IX and/or sepatate a resulting mixture of isomers into the individual isomers and/or convert a resulting salt into the free compound of the formula IX and/or into another salt and/or convert a resulting free compound of the formula IX into a salt to correspond to the above definition;

or D) a compound of formula X, optionally as an individual stereo isomer,

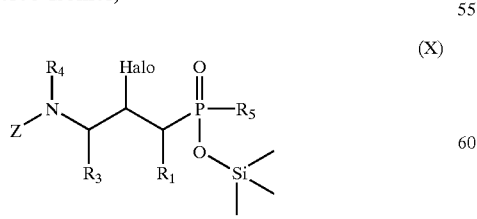

(X)

in which $R_1$, $R_3$, $R_4$ and $R_5$ are as defined in formula I, Z is a protecting group such as t-butyloxycarbonyl and Halo is a halogen atom, which compound of formula X may have been synthesized by a substitution reaction according to Scheme 4 employing an electrophilic compound in which $R_1$, $R_3$ and $R_4$ are as defined above, L is a leaving group such as iodo, Z and Halo are as defined above, and an activated by O-silylation methyl phosphinic acid derivative in which $R_5$ is as defined above, Scheme 4

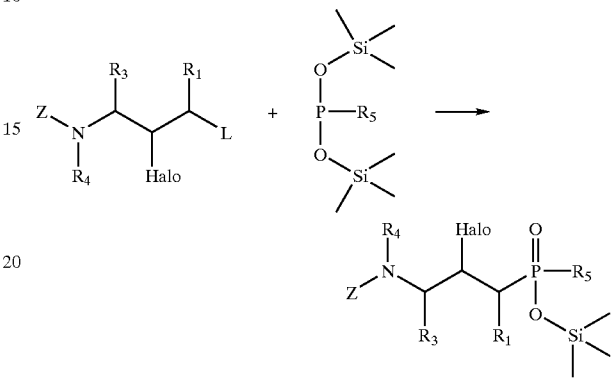

is converted by a hydrolytic reaction to a compound of formula VI

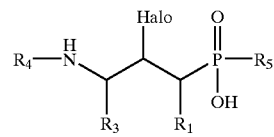

(VI)

wherein $R_1$, $R_3$, $R_4$ and $R_5$ are as defined above in formula I, and optionally convert the above resulting compound VI into another chemical compound of the formula VI and/or sepatate a resulting mixture of isomers into the individual isomers and/or convert a resulting salt into the free compound of the formula VI and/or into another salt and/or convert a resulting free compound of the formula VI into a salt to correspond to the above definition;

or E) a compound of formula XI, optionally as an individual stereo isomer,

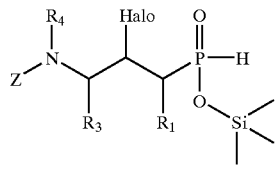

(XI)

in which $R_1$, $R_3$ and $R_4$ are as defined in formula I, Z is a protecting group such as t-butyloxycarbonyl and Halo is a halogen atom, which compound of formula XI may have been synthesized by a substitution reaction according to Scheme 5 employing an electrophilic compound in which $R_1$, $R_3$ and $R_4$ are as defined above, L is a leaving group such as iodo, Z and Halo are as defined above, and phosphinic acid activated by O-silylation,

Scheme 5

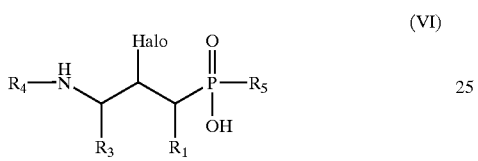

is converted by a hydrolytic reaction and then a P-alkylation reaction to a compound of formula VI

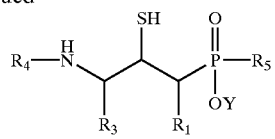
(VI)

wherein $R_1$, $R_3$, $R_4$ and $R_5$ are as defined above in formula I, and optionally convert the above resulting compound VI into another chemical compound of the formula VI and/or sepatate a resulting mixture of isomers into the individual isomers and/or convert a resulting salt into the free compound of the formula VI and/or into another salt and/or convert a resulting free compound of the formula VI into a salt to correspond to the above definition;

or F) a compound of formula XII

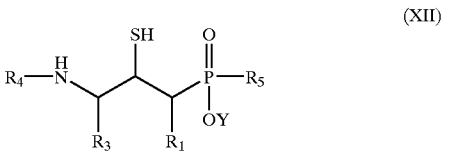
(XII)

in which $R_1$, $R_3$, $R_4$ and $R_5$ are as defined above in formula I, and Y is hydrogen or a protecting group such as lower alkyl, which compound of formula XII may have been synthesized by an addition reaction according to Scheme 6 treating an unsaturated phosphinic acid derivative, in which $R_1$, $R_3$, $R_4$ and $R_5$ are as defined above in formula I, with $H_2S$, a mercaptide ion ($HS^-$) or a protected mercapto compound such as benzyl thiol in which case the protective group thereafter is removed

Scheme 6

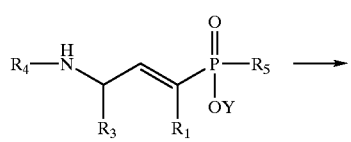

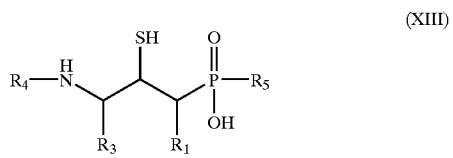

is converted by a hydrolytic reaction to a compound of formula XIII, (XIII)

in which $R_1$, $R_3$, $R_4$ and $R_5$ are as defined above in formula I, and optionally convert the above resulting compound XIII into another chemical compound of the formula XIII and/or sepatate a resulting mixture of isomers into the individual isomers and/or convert a is resulting salt into the free compound of the formula XIII and/or into another salt and/or convert a resulting free compound of the formula XIII into a salt to correspond to the above definition;

The invention will now be described more in detail by the following examples which are not to be construed as limiting the invention.

EXAMPLES

Example 1

(3-Amino-2-fluoropropyl)(methyl)phosphinic Acid

To a solution of $BH_3$-THF (1 M, 22.2 mL, 22.2 mmol) at 0° C. was added a solution of ethyl (3-amino-2-fluoro-3-oxopropyl)(methyl)phosphinate (2.00 g, 10.1 mmol) in THF (15 mL). The resulting solution was heated to reflux for 2 h. The solution was cooled to room temperature and 6 N HCl (60 mL) was added slowly. The THF was removed by evaporation in vacuo and another portion of 6 N HCl (20 mL) was added. The solution was heated to reflux for 2.5 h, cooled to room temperature and evaporated. The residue was purified by ion-exchange chromatography (DOWEX® 50WX 8-200, $H^+$ form, 3.5×4.0 cm). The resin was prewashed with 1:1 methanol/water (200 mL). The crude product was dissolved in 1:1 methanol/water and loaded onto the column. The column was washed with 1:1 methanol/water (400 mL). The eluent was changed to 2:1:1 methanol/water/concentrated ammonium hydroxide. Two fractions (150 mL) were combined and evaporated to give 1.28 g of a sticky oil. The residue was purified by chromatography on a wet-packed silica gel column (4×28 cm) eluting with 50:50:1 methanol/methylene chloride/ammonium hydroxide. The appropriate fractions were combined and evaporated to give 730 mg (46%) of (3-amino-2-fluoropropyl)(methyl)phosphinic acid as a white solid. Data: mp 78–84° C.; $R_f$=0.26 (60:40:1 methanol, methylene chloride, concentrated ammonium hydroxide); $^1H$ NMR (300 MHz, $D_2O$) δ5.01 (dm, J=49.5 Hz, 1H), 3.09–3.32 (m, 2H), 1.76–2.18 (m, 2H), 1.28 (d, J=14 Hz); $^{13}C$ NMR (75 MHz, $D_2O$+Dioxane) δ91.3 (d, J=169 Hz), 47.1 (d, J=12 Hz), 37.2 (dd, J=20.9, 89 Hz), 19.8 (d, J=95 Hz); APIMS: m/z=156 $(M+H)^+$.

Example 2

(3-Amino-2-fluoro-1-methylpropyl)(methyl) phosphinic Acid

To an ice bath cooled solution of ethyl 3-amino-2-fluoro-1-methyl-3-oxopropyl(methyl)phosphinate (2.1 g, 10 mmol)

in THF (25 ml) was added 1 M BH₃-THF (23 mL, 23 mmol) while under an argon atmosphere. After 10 minutes, the solution was heated to reflux for 2 h. The solution was cooled to room temperature and 6 N HCl (30 mL) was added dropvise. The THF was removed by rotovap and another portion of 6 N HCl (30 mL) was added. The mixture was refluxed for 2 h and then stirred at room temperature over night. The solution was cooled, evaporated, co-evaporated with water and then with etanol. The residue was dissolved in methanol (25 mL) an d then propyleneoxide (4 mL) was added dropvise. After 3 hours at room temperature the solution was concentrated and the product purified by chromatography on a wet-packed silica gel column eluting with water/methanol (2%–4% water). The appropriate fractions were combined and evaporated to give an oil which precipitated when diethyl ether was added. The product was isolated by filtration and there was obtained 580 mg (35%) of a diastereomeric mixture of (3-amino-2-fluoro-1-methylpropyl)(methyl)phosphinic acid as a white solid. $^1$H NMR (400 MHz, D$_2$O) δ4.8–5.2 (m, 1H), 3.2–3.5 (m, 2H), 1.8–2.2 (m, 1H), 1.0–1.3 (m, 6H); MS: m/z=170 (M+H)$^+$.

Example 3

(2R)-(3-Amino-2-fluoropropyl)(methyl)phosphinic Acid

A suspension of compound (2R)-(3-amino-2-fluoropropyl)phosphinic acid (1.0 g, 7.1 mmol) in HMDS (7.47 mL, 35.4 mmol) was heated to reflux for 16 h. The reaction was cooled to room temperature, treated with diglyme (8.0 mL) and heated to reflux for 6 h. After the mixture was cooled to room temperature , Hünig's base (1.23 mL, 7.1 mmol) was added followed by dropwise addition of methyl iodide (1.32 mL, 21.2 mmol). The reaction was stirred for 23.5 h then it was diluted with methylene chloride and extracted with 2 N HCl solution. The aqueous layer was washed with methylene chloride and diethyl ether and then evaporated under reduced pressure. The crude product was passed through a Dowex 50WX8-200 mesh H$^+$ form column eluting, with 1:1 methanol/water until no further material was detected by TLC analysis. The product was then eluted with 1:3 concentrated ammonium hydroxide solution/methanol. Further purification by column chromatography on silica gel eluting with methylene chloride, methanol, concentrated ammonium hydroxide solution (6:3:1) afforded (2R)-(3-amino-2-fluoropropyl)(methyl)phosphinic acid as a white solid (720 mg, 65%). $^1$H NMR (300 MHz, D$_2$O) δ5.20 (m, 0.5H), 5.03 (m, 0.5H), 3.20–3.42 (m, 2H), 1.80–2.22 (m, 2H), 1.30 (d, J=14.0 Hz, 3H).

Example 4

(2S)-(3-Amino-2-fluoropropyl)(methyl)phosphinic Acid

A suspension of compound (2S)-(3-amino-2-fluoropropyl)phosphinic acid (1.2 g, 8.5 mmol) in HMDS (8.96 mL, 42.4 mmol) was heated to reflux for 15 h. The reaction was cooled to room temperature, treated with diglyme (9.6 mL) and heated to reflux for 7 h. After the mixture was cooled to room temperature, Hünig's base (1.47 mL, 8.4 mmol) was added followed by dropwise addition of methyl iodide (1.58 mL, 25.4 mmol). The reaction was stirred overnight then it was diluted with methylene chloride and extracted with 2 N HCl solution. The aqueous layer was washed with methylene chloride and diethyl ether and then evaporated under reduced pressure. The crude product was passed through a Dowex 50WX8-200 mesh H$^+$ form column eluting with 1:1 methanol/water until no further material was detected by TLC analysis. The product was then eluted with 1:3 concentrated ammonium hydroxide solution/methanol. Further purification by column chromatography on silica gel eluting with methylene chloride, methanol, concentrated ammonium hydroxide solution (6:3:1) afforded (2S)-(3-amino-2-fluoropropyl)(methyl)phosphinic acid as a white solid (504 mg, 38%). $^1$H NMR (300 MHz, D$_2$O) δ5.20 (m, 0.5H), 5.03 (m, 0.5H), 3.20–3.42 (m, 2H), 1.80–2.22 (m, 2H), 1.30 (d, J=14.0 Hz, 3H).

Intermediates

Example I1

Ethyl 3-[ethoxy(methyl)phosphoryl]-2-fluoropropanoate (Intermediate to the Compound According to the Example 1)

Ethyl methylphosphinate (12.8 g, 118 mmol) was refluxed with 1,1,1,3,3,3-hexamethyldisilazane (HMDS) (24.9 mL, 118 mmol) for 2 h while under an argon atmosphere. The solution was cooled to room temperature and then fluoroacrylate (13.3 g, 113 mmol) was added to the solution. After stirring at room temperature for 60 h while under an argon atmosphere, the mixture was diluted with methylene chloride (200 mL) and washed with 1 N HCl (200 mL). The aqueous layer was extracted with methylene chloride (200 mL). The combined organic layers were washed with brine (150 mL), dried over Na$_2$SO$_4$, filtered, and evaporated to give 20.0 g of an oil. The residue was chromatographed on a wet-packed silica gel column (7.5×40 cm) eluting with 95:5 methylene chloride/methanol. The appropriate fractions were combined and evaporated to give 12.6 g (50%) of ethyl 3-[ethoxy(methyl)phosphoryl]-2-fluoropropanoate as a yellow oil. Data: $^1$H NMR (300 MHz, CDCl$_3$) δ5.11–5.43 (m, 1H), 4.23–4.34 (m, 2H), 4.03–4.19 (m, 2H), 2.26–2.53 (m, 2H), 1.58 (d, J=14 Hz, 3H), 1.28–1.39 (m, 3H).

Example I2

Ethyl (3-amino-2-fluoro-3-oxopropyl)(methyl) phosphinate (Intermediate to the Compound According to the Example 1)

A solution of ethyl 3-[ethoxy(methyl)phosphoryl]-2-fluoropropanoate (12.6 g, 55.6 mmol), ethanol (15 mL), and concentrated ammonium hydroxide (14.8 N, 5.6 mL, 83 mmol) were stirred at room temperature for 16 h. The solvent was evaporated and the residue chromatographed on a wet-packed silica gel column (5.5×31 cm) eluting with 90:10 methylene chloride/methanol. The appropriate fractions were combined and evaporated to give 9.5 g (86%) of ethyl (3-amino-2-fluoro-3-oxopropyl)(methyl)phosphinate as a clear oil. Data: $^1$H NMR (300 MHz, CDCl$_3$) δ6.62 (s, 1H), 6.33 (s, 1H), 5.10–5.42 (m, 1H), 4.02–4.18 (m, 2H), 2.19–2.70 (m, 2H), 1.60 (d, J=14 Hz, 3H), 1.34 (m, 3H)

Example I3

Ethyl 3-[ethoxy(methyl)phosphoryl]-2-fluorobutanoate (Intermediate to the Compound According to the Example 2)

A mixture of ethyl (methyl)phosphinate (3.2 g, 30 mmol) and 1, 1,1,3,3,3-hexamethyldisilazane (4.8 g, 30 mmol) was heated to reflux for 2 h under an argon atmosphere. The mixture was cooled to room temperature and a diastereomeric mixture of ethyl 2-fluorobut-2-enoate (4.0 g, 30 mmol) was added. The reagents were heated to 70° C. for three days and then at room temperature for 4 days under an argon atmosphere. The mixture was diluted with methylene chloride (200 mL). The solution was washed with 1 N HCl (200 mL) and the aqueous solution extracted with methylene chloride (200 mL). The combined organic solutions were washed with saturated sodium chloride, dried over $MgSO_4$, filtered and evaporated. The residue was purified by chromatography on a wet-packed silica gel column eluting with methylene chloride/methanol (99:1–97:3). The appropriate fractions were combined and evaporated to give 2.9 g (40%) of ethyl 3-[ethoxy(methyl)phosphoryl]-2-fluorobutanoate as a clear oil. $^1$H NMR (400 MHz, $CDCl_3$) δ4.8–5.6 (m, 1H), 4.2–4.4 (m, 2H), 4.0–4.2 (m, 2H), 2.4–2.6 (m, 1H), 1.1–1.5 (m, 12H).

Example I4

Ethyl 3-amino-2-fluoro-1-methyl-3-oxopropyl (methyl)phosphinate (Intermediate to the Compound According to the Example 2)

To a solution of ethyl 3-[ethoxy(methyl)phosphoryl]-2-fluorobutanoate (3.0 g, 12.4 mmol) in ethanol (15 mL) was added concentrated ammonium hydroxide (14.8 M, 1.3 mL, 19 mmol). The solution was stirred for 24 h at room temperature and then at 50° C. for 2 hours. Another portion of concentrated ammonium hydroxide (14.8 M, 0.5 mL, 7 mmol) was added and the mixture was stirred at room temperature for three days and then evaporated to give 2.4 g (91%) of a diastereomeric mixture of ethyl 3-amino-2-fluoro-1-methyl-3-oxopropyl(methyl)phosphinate as a clear oil. $^1$H NMR (400 MHz, $CDCl_3$) δ5.9–6.7 (m, 2H), 4.9–5.6 (m, 1H), 4.0–4.2 (m, 2H), 2.5–2.8 (m, 1H), 1.2–1.6 (m, 9H).

Example I5

(2R)-(3-Amino-2-fluoropropyl)phosphinic acid (Intermediate to the Compound According to the Example 3)

Ammonium hypophosphite (73.8 g, 0.89 mol) was added to 3 necked 2-L flask equipped with a mechanical stirrer, thermometer, addition funnel and an argon bubbler. The flask was placed in a water bath at room temperature and N,O-Bis-(trimethylsilyl)acetamide (215 mL, 0.87 mol-BSA) was added at such a rate that the internal temperature was maintained below 38° C. (30 minutes approx.) using ice cooling. Upon completing the addition of BSA, the reaction mixture was heated to 45–48° C. and maintained at this temperature for 1 h. The reaction was cooled to room temperature and a solution of tert-butyl (2R)-2-fluoro-3-iodopropylcarbamate (27.3 g, 0.09 mol) in methylene chloride (300 mL) was added to the reaction mixture. The reaction was then allowed to stir at room temperature for 18 h. The reaction mixture was cooled to 0° C. and was cautiously quenched with methanol (275 mL) and then with water (32 mL). The reaction mixture was stirred for 30 min after which the reaction was filtered and the solids were washed with methanol. The filtrate was concentrated and the residue placed under high vacuum (0.1 mm Hg) overnight. The crude residue was triturated with methylene chloride, methanol, concentrated ammonium hydroxide solution (80:20:1) and was filtered. The filtrate was concentrated under reduced pressure and the trituration was repeated. The crude concentrate was transferred to a 2-L flask, dissolved in methanol (375 mL) and placed in a water bath at room temperature. A saturated solution of hydrogen chloride gas in ethyl acetate (500 mL) was added and the mixture stirred for 3 h. The reaction mixture was filtered and the solids were washed with a mixture of methanol and ethyl acetate (90:10). The filtrate was concentrated under reduced pressure and the crude product was passed through a Dowex® 50WX8-200 mesh $H^+$ form (500 g, 8×15 cm) column eluting with 1:1 methanol/water until no further material was detected by TLC analysis. The requisite crude product was then eluted with 1:3 concentrated ammonium hydroxide solution/methanol. The product was further purified by column chromatography eluting with chloroform, methanol, concentrated ammonium hydroxide solution (6:3:1) to afford (2R)-(3-Amino-2-fluoropropyl)phosphinic acid as a white solid (3.12 g, 24%). $^1$H NMR (300 MHz, $D_2O$) δ7.90 (s, 0.5H), 6.15 (s, 0.5H), 5.12–5.29 (m, 0.5H), 4.9–5.10 (m, 0.5H), 3.12–3.42 (m, 2H), 1.74–2.26 (m, 2H).

Example I6

(2R)-3-(Dibenzylamino)-2-fluoro-1-propanol (Intermediate to the Compound According to the Example 3)

Lithium borohydride (5.3 g, 0.24 mol) was suspended in THF (200 mL) under a nitrogen atmosphere and cooled to −15° C. with stirring. Methyl (2R)-3-(dibenzylamino)-2-fluoropropanoate (56.6 g, 0.19 mol) was suspended in THF (250 mL) and added dropwise to the mixture over 1 h; the internal temperature was maintained below −10° C. during the addition. On completion of addition, the reaction mixture was allowed to warm to room temperature and stirred at this temperature for 17 h. The reaction mixture was cooled to 0° C. and cautiously quenched with a saturated aqueous solution of ammonium chloride (300 mL). The reaction mixture was extracted with ethyl acetate (2×200 mL) and the organic phase was concentrated under reduced pressure. The crude residue was dissolved in 2 N hydrochloric acid (200 mL, pH=2 approx.) and the aqueous phase was washed with ether (2×200 mL). The aqueous phase was basified (pH=10 approx.) with 80% ammonium hydroxide in brine, extracted with ethyl acetate (3×200 mL), dried over anhydrous sodium sulfate (10 g), filtered and concentrated under reduced pressure to afford (2R)-3-(dibenzylamino)-2-fluoro-1-propanol (48 g, 93%) as a yellow oil. $^1$H NMR (300 MHz, $CDCl_3$) δ7.15–7.38 (m, 10H), 4.65–4.78 (m, 0.5H), 4.48–4.58 (m, 0.5H), 3.50–3.82 (m, 6H), 2.70–2.88 (m, 2H).

Example I7

(2R)-3-Amino-2-fluoro-1-propanol (Intermediate to the Compound According to the Example 3)

(2R)-3-(dibenzylamino)-2-fluoro-1-propanol (29.2 g, 0.11 mol) was dissolved in ethanol (300 mL). 10 wt. % Palladium (II) hydroxide on carbon (5.0 g) was added and the mixture placed on a Parr® shaker and shaken under a hydrogen atmosphere (55 psi) for 6 h. When no further hydrogen uptake was observed, the mixture was filtered through a pad of Celite® (20 g). A fresh batch of palladium (II) hydroxide (5 g) was added to the ethanol mixture and re-subjected to the hydrogenation conditions described above for 17 h. The crude reaction mixture was filtered through Celite® and concentrated under reduced pressure to afford (2R)-3-amino-2-fluoro-1-propanol as a pale yellow oil (9.6 g, 96%). $^1$H NMR (300 MHz, $CD_3OD$) δ4.78–5.00 (br s, 3H), 4.49–4.62 (m, 0.5H), 4.32–4.46 (m, 0.5H), 3.54–3.70 (m, 2H), 2.70–2.96 (m, 2H).

Example I8

Tert-butyl (2R)-2-fluoro-3-hydroxypropylcarbamate (Intermediate to the Compound According to the Example 3)

(2R)-3-amino-2-fluoro-1-propanol (4.6 g, 49 mmol) was dissolved in 25% aqueous dioxane (160 mL), potassium carbonate (7.1 g, 51 mmol) was added and the mixture cooled to 0° C. Di-tert-butyl dicarbonate (11.6 g, 53 mmol) was added in two portions. The mixture was then allowed to warm to room temperature overnight. The crude reaction mixture was concentrated to dryness, water (150 mL) was added followed by saturated aqueous potassium hydrogen sulfate (until pH=3 approx.). The organic material was extracted with methylene chloride (2×150 mL), dried over sodium sulfate, filtered and concentrated under reduced pressure to afford tert-butyl (2R)-2-fluoro-3-hydroxypropylcarbamate (9.5 g, 100%) as a colorless oil. $^1$H NMR (300 MHz, CDCl$_3$) δ4.82–5.04 (br s, 1H), 4.62–4.72 (m, 0.5H), 4.48–4.58 (m, 0.5H), 3.62–3.72 (m, 2H), 3.32–3.62 (m, 2H), 3.20–3.44 (br s, 1H), 1.48 (s, 9H).

Example I9

Tert-butyl (2R)-2-fluoro-3-iodopropylcarbamate
(Intermediate to the Compound According to the Example 3)

Imidazole (26.6 g, 0.39 mol) was dissolved in methylene chloride (400 mL) at room temperature. Iodine (102.5 g, 0.39 mol) was added and the reaction mixture was stirred for 10 min at room temperature and then cooled to 0° C. Triphenylphosphine (102.5 g, 0.39 mol) was added portionwise over 10 min such that the internal temperature remained below 10° C. A solution of tert-butyl (2R)-2-fluoro-3-hydroxypropylcarbamate (60.4 g, 0.31 mol) in methylene chloride (100 mL) was added dropwise. On completion of addition of tert-butyl (2R)-2-fluoro-3-hydroxypropylcarbamate, additional methylene chloride (200 mL) was added. The reaction mixture was allowed to warm to room temperature and stirring was continued for 17 h. The reaction mixture was filtered through a pad of Celite® (50 g) and washed with additional methylene chloride. The filtrate was concentrated under reduced pressure and purified by silica gel column chromatography eluting with methylene chloride. This procedure afforded tert-butyl (2R)-2-fluoro-3-iodopropylcarbamate as a white solid (64.7 g, 68%). $^1$H NMR (300 MHz, CDCl$_3$) δ4.80–5.10 (br s, 1H), 4.58–4.72 (m, 0.5H), 4.42–4.56 (m, 0.5H), 3.48–3.70 (m, 1H), 3.20–3.46 (m, 3H), 1.48 (s, 9H).

Example I10

(2S)-(3-Amino-2-fluoropropyl)phosphinic Acid
(Intermediate to the Compound According to the Example 4)

Ammonium hypophosphite (58.1 g, 0.70 mol) was added to a 3 necked 2-L flask equipped with a mechanical stirrer, thermometer, addition funnel and an argon bubbler. N,O-Bis-(trimethylsilyl)acetamide (175.9 mL, 0.71 mol -BSA) was added at such a rate that the internal temperature was maintained between 35–40° C. Upon completing the addition of BSA, the reaction mixture was maintained at 35–40° C. for 45 min. Methylene chloride (150 mL) was added and the mixture was stirred at 35–40° C. for an additional 45 min. The reaction was cooled to room temperature and a solution of tert-butyl (2S)-2-fluoro-3-iodopropylcarbamate (42.5 g, 0.14 mol) in methylene chloride (300 mL) was added to the reaction mixture. The reaction was then allowed to stir at room temperature overnight. The reaction mixture was cooled to 0° C. and was cautiously quenched with methanol (150 mL) and then with water (60 mL). The reaction was concentrated and the residue placed under high vacuum (0.1 mm Hg). The residue was adjusted to approximately pH 8 by the addition of concentrated ammonium hydroxide (50 mL) then methylene chloride (400 mL) and methanol (250 mL) were added. The resulting solids were filtered and the filtrate was concentrated. The residue was triturated with methylene chloride, methanol, concentrated ammonium hydroxide solution (80:20:1; 400 mL) and was filtered. The filtrate was concentrated under reduced pressure and the crude concentrate was dissolved in methanol (400 mL). A saturated solution of hydrogen chloride gas in ethyl acetate (600 mL) was added and the mixture stirred for 3 h. The reaction mixture was filtered and the filtrate was concentrated under reduced pressure. The crude product was passed through a Dowex® 50WX8-200 mesh H$^+$ form (450 g) column eluting with 1:1 methanol/water until no further material was detected by TLC analysis. The requisite crude product was then eluted with 1:3 concentrated ammonium hydroxide solution/methanol. The product was further purified by column chromatography eluting with methylene chloride, methanol, concentrated ammonium hydroxide solution (6:3:1) to afford (2S)-(3-amino-2-fluoropropyl) phosphinic acid as a white solid (3.46 g, 17%). $^1$H NMR (300 MHz, D$_2$O) δ7.90 (s, 0.5H), 6.15 (s, 0.5H), 5.12–5.29 (m, 0.5H), 4.92–5.10 (m, 0.5H), 3.12–3.42 (m, 2H), 1.74–2.

Example I11

Methyl (2S)-3-(dibenzylamino)-2-fluoropropanoate
(Intermediate to the Compound According to the Example 4)

Methyl (2R)-2-(dibenzylamino)-3-hydroxypropanoate (231.7 g, 0.77 mol) was dissolved in THF (850 mL) and a solution of DAST (196 g, 1.2 mol) in THF (400 mL) was added slowly dropwise. Once the addition was complete, the reaction was stirred for an additional 1.5 h. TLC analysis indicated consumption of starting material. The reaction was then cooled to 0° C. and was quenched by the slow addition of water (1.5l) followed by neutralization by the addition of solid sodium bicarbonate. Once neutral, a 1:1 mixture of concentrated ammonium hydroxide/saturated sodium chloride solution was added and the reaction was extracted with ethyl acetate and concentrated under reduced pressure. The crude mixture was purified by silica gel column chromatography eluting with ethyl acetate, hexanes (1:4) to provide the desired compound (188.3 g, 62%) as an oil. $^1$H NMR (300 MHz, CDCl$_3$) δ7.18–7.38 (m, 10H), 5.12–5.17 (m, 0.5H), 4.95–5.00 (m, 0.5H), 3.81–3.87 (m, 2H), 3.69 (s, 3H), 3.49–3.55 (m, 2H), 2.90–3.12 (m, 2

Example I12

(2S)-3-(Dibenzylamino)-2-fluoro-1-propanol
(Intermediate to the Compound According to the Example 4)

Lithium borohydride (17.7 g, 0.81 mol) was suspended in THF (400 mL) under a nitrogen atmosphere and cooled to −15° C. with stirring. Methyl (2S)-3-(dibenzylamino)-2-fluoropropanoate (188.3 g, 0.62 mol) was suspended in THF (400 mL) and added dropwise to the mixture. On completion of addition, the reaction mixture was allowed to warm to room temperature and stirred at this temperature for 3 h. TLC analysis indicated complete consumption of starting material. The reaction mixture was cooled to 0° C. and cautiously quenched with a saturated aqueous solution of ammonium chloride (300 mL). Additional water (400 mL) was added then the reaction mixture was extracted with ethyl acetate and the organic phase was concentrated under reduced pressure. The crude residue was dissolved in 2 N hydrochloric acid and the aqueous phase was washed twice with ether. The aqueous phase was basified (pH=10 approx.) with 80% ammonium hydroxide in brine, extracted with ethyl acetate, dried over anhydrous sodium sulfate, filtered and concentrated under reduced pressure to afford (2S)-3-(dibenzylamino)-2-fluoro-1-propanol (156.6 g, 92%) as a yellow oil. $^1$H NMR (300 MHz, CDCl$_3$) δ7.15–7.38 (m, 10H), 4.65–4.78 (m, 0.5H), 4.48–4.58 (m, 0.5H), 3.50–3.82 (m, 6H), 2.70–2.88 (m, 2H).

Example I13

(2S)-3-Amino-2-fluoro-1-propanol (Intermediate to the Compound According to the Example 4)

(2S)-3-(dibenzylamino)-2-fluoro-1-propanol (39.1 g, 0.14 mol) was dissolved in ethanol (300 mL). 10 wt. % Palladium (II) hydroxide on carbon (5.0 g) was added and the mixture placed on a Parr® shaker and shaken under a hydrogen atmosphere (55 psi) overnight. When no further hydrogen uptake was observed, the mixture was filtered through a pad of Celite®. A fresh batch of palladium (II) hydroxide (5 g) was added to the ethanol mixture and re-subjected to the hydrogenation conditions described above for 12 h. Again, when no further hydrogen uptake was observed, the mixture was filtered through a pad of Celite®. A fresh batch of palladium (II) hydroxide (5 g) was added to the ethanol mixture and re-subjected to the hydrogenation conditions described above for 12 h. The crude reaction mixture was filtered through Celite® and concentrated under reduced pressure to afford (2S)-3-amino-2-fluoro-1-propanol as a pale yellow oil (13.3 g, 100%). $^1$H NMR (300 MHz, CD$_3$OD) δ4.78–5.00 (br s, 3H), 4.49–4.62 (m, 0.5H), 4.32–4.46 (m, 0.5H), 3.54–3.70 (m, 2H), 2.70–2.96 (m, 2H).

Example I14

Tert-butyl (2S)-2-fluoro-3-hydroxypropylcarbamate (Intermediate to the Compound According to the Example 4

(2S)-3-amino-2-fluoro-1-propanol (38.6 g, 0.41 mol) was dissolved in 25% aqueous dioxane (1.4 L), potassium carbonate (60.1 g, 0.43 mol) was added followed by di-tert-butyl dicarbonate (99.5 g, 0.46 mol). The mixture was stirred overnight. TLC analysis indicated complete consumption of starting material. The crude reaction mixture was concentrated to dryness, water (300 mL) was added followed by saturated aqueous potassium hydrogen sulfate (until pH=3 approx.). The organic material was extracted twice with methylene chloride, dried over sodium sulfate, filtered and concentrated under reduced pressure to afford tert-butyl (2S)-2-fluoro-3-hydroxypropylcarbamate (79.5 g, 99%) as a pale yellow oil. $^1$H NMR (300 MHz, CDCl$_3$) δ4.82–5.04 (br s, 1H), 4.62–4.72 (m, 0.5H), 4.48–4.58 (m, 0.5H), 3.62–3.72 (m, 2H), 3.32–3.62 (m, 2H), 3.20–3.44 (br s, 1H), 1.48 (s, 9H).

Example I15

Tert-butyl (2S)-2-fluoro-3-iodopropylcarbamate (Intermediate to the Compound According to the Example 4)

Imidazole (19.8 g, 0.29 mol) was dissolved in methylene chloride (900 mL) at room temperature. Iodine (73.9 g, 0.29 mol) was added and the reaction mixture was stirred for 10 min at room temperature and then cooled to 0° C. Triphenylphosphine (76.3 g, 0.29 mol) was added portionwise over 10 min such that the internal temperature remained below 10° C. A solution of tert-butyl ($^2$S)-2-fluoro-3-hydroxypropylcarbamate (45.0 g, 0.23 mol) in methylene chloride (300 mL) was added dropwise. The reaction mixture was allowed to warm to room temperature and stirring was continued for 12 h. The reaction mixture was filtered through a pad of Celite® and washed with additional methylene chloride. The filtrate was concentrated under reduced pressure and purified by silica gel column chromatography eluting with methylene chloride. This procedure afforded tert-butyl (2S)-2-fluoro-3-iodopropylcarbamate as a colorless oil (42.5 g, 62%). $^1$H NMR (300 MHz, CDCl$_3$) δ4.80–5.10 (br s, 1H), 4.58–4.72 (m, 0.5H), 4.42–4.56 (m, 0.5H), 3.48–3.70 (m, 1H), 3.20–3.46 (m, 3H), 1.48 (s, 9H).

Pharmaceutical Preparations

The compound according to formula (I) of the present invention can be used as an active ingredient in a pharmaceutical preparation for oral, rectal, epidural, intravenous, intramuscular, subcutanous, nasal administration and administration by infusion or for any other suitable route of administration. Preferably the way of administration is oral or by injection/infusion.

The pharmaceutical preparations contain a compound of the present invention in combination with one or more pharmaceutically acceptable ingredients. The finished dosage forms are manufactured by known pharmaceutical processes. Usually the amount of active compounds is between 0.1–95% by weight of the preparation, preferably between 0.2–20% by weight in preparations for parenteral use and preferably between 1–50% by. weight in preparations for oral administration.

In the preparation of pharmaceutical preparations containing a compound of the present invention in the form of solid dosage units for oral administration, the compound selected may be mixed with solid, powdered pharmaceutically acceptable ingredients (among these for instance disintegrating agents and lubricating agents). The mixture is then processed into granules, tablets, capsules or sachets.

Dosage units for rectal administration may be prepared in the form of suppositories; in the form of a gelatine rectal capsule; in the form of a ready-made micro enema; or in the form of a dry micro enema formulation to be reconstituted in a suitable solvent just prior to administration.

Liquid preparations for oral administration may be prepared in the form of syrups or suspensions, or in the form of a dry mixture to be reconstituted with a suitable solvent prior to use.

Solutions for parenteral administration may be prepared as a solution of a compound of the invention in a pharmaceutically acceptable solvent and are dispensed into unit doses in the form of ampoules or vials. They may also be prepared as a dry preparation to by reconstituted with a suitable solvent extemporaneously before use.

The typical daily dose of the active compound will depend on various factors such as for example the individual requirement of each patient, the route of administration and the disease. In general, dosages will be in the range of 1 μg to 100 mg per day and kg body weight, preferably 10 μg to 20 mg per day and kg body weight.

Biological Studies

[$^3$H]GABA Radioligand Binding Assay

Rat synaptic membranes were prepared from the whole brain of Sprague Dawley male rats essentially as described previously (Zukin, et al. (1974) Proc. Natl. Acad. USA 71, 4802–4807). The [$^3$H]GABA competition assay, modified from Olpe et al ((1990) Eur. J. Pharmacol. 187, 27–38), was performed in 200 µl TCI (Tris Calcium Isoguvacine) buffer (50 mM Tris (tri(hydroxymethyl)aminomethane), pH 7.4, 2.5 mM CaCl$_2$ and 40 µM isoguvacine) containing 20 nM [$^3$H]GABA (specific activity: 3 Tera Becquerel (TBq)/ mmol), test compound or solvent and 80 µg synaptic membrane protein using 96-well plates. After incubation for 12–20 min at room temperature, incubations were terminated by rapid filtration through a glass fiber filter (Printed filtermat B filters, Wallac), which had been pretreated with 0.3% polyethyleneimine, using a 96-well plate cell harvester (Skatron or Tomtec). The filters were washed with buffer containing 50 mM Tris (tris(hydroxymethyl)aminomethane) and 2.5 mM CaCl$_2$ pH 7.4, at 4° C. and then dried at 55° C. MeltiLex B/HS scintillator sheet (Wallac) was melted onto the filter, and radioactivity was determined in a Microbeta scintillation counter (Wallac).

Results and Discussion

The compounds of the present invention were found to have surprisingly high affinities and potencies for the GABA$_B$ receptor as revealed by low IC$_{50}$ and EC$_{50}$ in the binding and ileum assays, respectively. The potencies with regard to inhibition of TLOSR were related to the affinity for, and activity on, the GABA$_B$ receptor. CNS side-effects (as measured by reduction in body temperature in the mouse) were only seen at doses higher than the therapeutic doses inhibiting TLOSR in the dog model. Therefore, the difference between therapeutic dose (inhibition of TLOSR) and dose causing side-effects was unexpectedly high.

What is claimed is:

1. A compound according to formula I

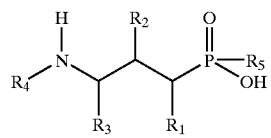

(I)

or a racemate, a stereoisomer or a mixture thereof, wherein:
R$_1$ represents hydrogen or lower alkyl;
R$_2$ represents a fluoro group;
R$_3$ represents hydrogen;
R$_4$ represents hydrogen; and
R$_5$ represents methyl, fluoromethyl, difluoromethyl, or trifluoromethyl; and
wherein the compound, racemate or a stereoisomer thereof may exist in the form of a pharmaceutically acceptable salt and/or solvate thereof.

2. The compound according to claim 1 which is (3-amino-2-fluoropropyl)(methyl)phosphinic acid.

3. The compound according to claim 2 which is (2R)-(3-amino-2-fluoropropyl)(methyl)phosphinic acid.

4. A compound according to claim 2 which is (2S)-(3-amino-2-fluoropropyl)(methyl)phosphinic acid.

5. A compound according to claim 1 which is (3-amino-2-fluoro-1-methylpropyl)(methyl)phosphinic acid.

6. A method for the inhibition of transient lower oesophageal sphincter relaxations which method comprises administering to a subject suffering from said condition a pharmaceutical preparation comprising a compound according to any one of claims 1–5.

7. A method for the treatment of gastro-oesophaegeal reflux disease which method comprises administering to a subject suffering from said condition a pharmaceutical preparation comprising a compound according to any one of claims 1–5.

8. A method for the treatment of regurgitation in infants which method comprises administering to a subject suffering from said condition a pharmaceutical preparation comprising a compound according to any one of claims 1–5.

9. A method for the treatment of GORD- or non-GORD-related asthma, belching, coughing, pain, cocaine addiction, hiccups, IBS, dyspepsia, emesis or nociception which method comprises administering to a subject suffering from said condition a pharmaceutical preparation comprising a compound according to any one of claims 1–5.

10. A pharmaceutical formulation comprising as active ingredient a therapeutically acceptable amount of a compound defined in any one of claims 1–5 optionally in association with diluents, excipients or inert carriers.

11. A compound selected from the group consisting of:
ethyl 3-[ethoxy(methyl)phosphoryl]-2-fluoropropanoate;
ethyl (3-amino-2-fluoro-3-oxopropyl)(methyl) phosphinate;
ethyl 3-[ethoxy(methyl)phosphoryl]-2-fluorobutanoate;
ethyl 3-amino-2-fluoro-1-methyl-3-oxopropyl(methyl) phosphinate;
(2R)-(3-amino-2-fluoropropyl)phosphinic acid;
(2R)-3-(dibenzylamino)-2-fluoro-1-propanol;
(2R)-3-amino-2fluoro-1-propanol;
tert-butyl (2R)-2-fluoro-3-hydroxypropylcarbamate;
tert-butyl (2R)-2-fluoro-3-iodopropylcarbamate;
(2S)-(3-amino-2-fluoropropyl)phosphinic acid;
methyl (2S)-3-(dibenzylamino)-2-fluoropropanoate;
(2S)-3-(dibenzylamino)-2-fluoro-1-propanol;
(2S)-3-amino-2-fluoro-1-propanol;
tert-butyl (2S)-2-fluoro-3-hydroxypropylcarbamate; and
tert-butyl (2S)-2-fluoro-3-iodopropylcarbamate.

* * * * *

UNITED STATES PATENT AND TRADEMARK OFFICE
CERTIFICATE OF CORRECTION

PATENT NO.     : 6,596,711 B1
DATED          : July 22, 2003
INVENTOR(S)    : Guzzo et al.

It is certified that error appears in the above-identified patent and that said Letters Patent is hereby corrected as shown below:

<u>Title page,</u>
Item [12], delete "Amin et al." and substitute therefore -- Guzzo et al. --
Item [75], delete "Kosrat Amin, Thomas Elebring, and Thomas Olsson".

Signed and Sealed this

Thirtieth Day of December, 2003

JAMES E. ROGAN
*Director of the United States Patent and Trademark Office*